US006568530B2

(12) United States Patent
Takahashi et al.

(10) Patent No.: US 6,568,530 B2
(45) Date of Patent: May 27, 2003

(54) INFORMATION LABEL FOR TARGET USER, AND DISPLAY PACKAGE HAVING THE LABEL

(75) Inventors: Tsuyoshi Takahashi, Tokyo (JP); Yuko Fukui, Tokyo (JP); Takeo Fujii, Tokyo (JP); Nobuko Uchibori, Tokyo (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/845,276

(22) Filed: May 1, 2001

(65) Prior Publication Data

US 2002/0088732 A1 Jul. 11, 2002

(30) Foreign Application Priority Data

Jan. 9, 2001 (JP) ......................................... 2001-001933

(51) Int. Cl.7 ............................. B65D 85/00; G09F 7/00
(52) U.S. Cl. ........................... 206/440; 15/215; 40/584; 206/459.5; 283/81
(58) Field of Search .............................. 206/204, 459.5, 206/494, 579, 440, 438; 15/215, 216; 40/584; 283/74, 75, 81

(56) References Cited

U.S. PATENT DOCUMENTS

| D244,914 S | * | 7/1977 | Nicol | 206/459.5 |
|---|---|---|---|---|
| 4,204,705 A | * | 5/1980 | Gordon et al. | 283/74 |
| 4,336,754 A | * | 6/1982 | Loeb | 283/74 |
| 4,887,845 A | * | 12/1989 | Nagai | 283/81 |
| 5,028,468 A | * | 7/1991 | Taylor | 428/71 |
| 5,549,940 A | * | 8/1996 | Noone | 206/579 |
| 5,967,665 A | * | 10/1999 | MacDonald et al. | 206/494 |
| 6,113,148 A | * | 9/2000 | Koranda et al. | 283/81 |
| 6,268,854 B1 | * | 7/2001 | Borden et al. | 345/341 |

* cited by examiner

*Primary Examiner*—Jim Foster
(74) *Attorney, Agent, or Firm*—Wenderoth, Lind & Ponack, L.L.P.

(57) ABSTRACT

There is developed a label which enables purchasers or ordinary consumers to identify suitable commodity products at a glance, thereby providing facilities for consumers when they purchase commodity products. A target user information label section corresponding to a target user of paper diapers packed in a package is printed at a position conspicuous for ordinary consumers on the surface of the package, along with a tradename of the paper diapers. All target user designs corresponding to all target users of paper diapers to be handled as commodities are displayed as a single set in the information label section. A specific target user design corresponding to a target user of the paper diapers packed in the package is displayed greater in size than the other target user designs belonging to the set.

5 Claims, 11 Drawing Sheets

INFORMATION LABEL FOR TARGET USER, AND DISPLAY PACKAGE HAVING THE LABEL

BACKGROUND OF THE INVENTION

1. Field of the Invention

The present invention relates to an information label to be provided on a commodity product or disposed in a shop for making it easy for an elderly person to find a commodity product suitable for him/her, as well as to a package having the information label.

2. Background Art

Disposable undergarments for personal care purposes, such as paper diapers or disposable briefs, can be purchased at an ordinary retail shop. The amount of incorporated absorbent and the thickness of a product change slightly according to the personal mobility of the person who is to wear the disposable undergarment (e.g., the person can "walk," "walk with assistance," or "sit with assistance " or is "bedridden," hereinafter called simply "Walk," "Walk with assistance," "Sit with assistance," and "Bedridden"). In order to enable an ordinary consumer to identify such a difference, in some cases a label for specifying a target user of a product (a person for which a commodity product is suitable; that is, a target user) is placed on a package of a product.

Examples of such a "label" include target user designs into which statuses of persons, such as "Walk," "Walk with assistance," "Sit with assistance," or "Bedridden," are visually drawn, and such a design is labeled on a product. A set of target user designs corresponding to "Walk," "Walk with assistance," "Sit with assistance," or "Bedridden" are labeled on a package. A specific target user is specified through use of dark and light colors or a predetermined symbol (e.g., a triangle, a circle, or a double circle). Further, simple explanations (such as "Walk," "Walk with assistance," "Sit with assistance," and "Bedridden") are assigned to respective designs.

In fact, an elderly person cannot instantaneously identify a target user by use of the above-described related-art labels. This is particularly true in a case where similar products are arranged in a row on shelves (which are observed daily in a supermarket). If an ordinary consumer steps some distance away from shelves, he or she cannot instantaneously understand a target user of a product from only a related-art label. When an ordinary consumer selects a commodity product, it is common for the consumer to initially view the overall shelves at a slightly remote location. In light of this fact, it turns out that the related-art label fails to play a role as a target user identification label.

The related-art label is an unsurpassed inconvenience to a person who is physically handicapped to such an extent that he/she requires assistance from other persons (e.g., an elderly person who is severely weary or a person who is handicapped). Particularly when a label is taken as a target user identification sign for commodities related to personal care products, some of the related-art labels fail to fulfill the reason for their existence.

In this regard, for example, Japanese Patent Application Laid-Open No. 194272/1998 describes a legible label to be affixed to a package, thereby preventing a worker from causing an error during transport or distribution and assortment of merchandise. However, such a label is not intended for an ordinary consumer. Even when a commodity product having this label is placed on display shelves in a retail shop, the label yields no effect.

The present invention has been conceived to solve the drawbacks set forth and is aimed at developing labels (target user information labels) which enable purchasers or ordinary consumers (particularly, persons who are handicapped to such an extent that they require assistance from another person) to identify suitable commodity products at a glance, thereby providing facilities for the consumers when they purchase commodity products.

SUMMARY OF THE INVENTION

To achieve such an object, the present invention provides an information label for target user (hereinafter referred to simply as a "target user information label") comprising a set of target user designs which symbolically illustrate target users, wherein a target user design symbolically illustrating a target user of a commodity product is drawn greater in size than other target user designs, more preferably in another color and along with an explanatory notice to be appended to solely the target user design.

When there are commodities of the same type or analogous commodities whose target users are different, the target user information label according to the present invention clearly points at a corresponding target user. As a result, an ordinary consumer can very easily find desired commodities from among the commodities arranged on display.

More specifically, the present invention provides the following labels.

(1) A target user information label which is to be used for commodities of the same type or analogous commodities whose target users are different and which comprises a set of target user designs symbolically illustrating the target users, wherein a predetermined target user design of the set is displayed greater in size than the other target user designs.

According to the invention described in (1), the "target user information label" is formed as a set of target user designs. As a result, a person who attempts to purchase a desired commodity from among commodities of the same type or analogous commodities whose target users are different can perceive categories of commodities as a single pattern. Further, a corresponding target user design of the set is drawn greater in size than the other target user designs. Consequently, the consumer can find a target user design corresponding to a target user of a commodity at a glance from among the overall commodities. Thus, there is prevented erroneous purchase of a commodity, which would otherwise be caused by misidentification. Even when a user asks a care-giver to purchase a commodity, the user can easily specify a desired commodity, thus-affording great convenience to the user.

Even when a user views commodities from a slightly remote location, the user can identify a desired commodity from the overall geometry of the set of target user designs (e.g., the location of a protuberance in the set of target user designs). Thus, the target user label matches the actual conditions under conditions from selection of a desired commodity to purchase of the thus-selected commodity product. In terms of convenience to an ordinary consumer, the target user label according to the present invention is more profitable than the related-art labels.

(2) Preferably, the target user information label described in (1) is appended to at least one selected from the group consisting of a "display package for packing commodities of the same type or analogous commodities whose target users are different," a "floor in the vicinity of a location where commodities of the same type or analogous commodities whose target users are different are to be placed for display," and an "article to be hung on shelves on which commodities of the same type or analogous commodities whose target users are different are to be arranged for display."

The invention described in (2) shows an embodiment of the target user information label described in (1). As a result of use of the target user information label described in (1), it becomes easy for a purchaser to identify a desired commodity from commodities of the same type or analogous commodities whose target users are different. By means of the invention described in (2), the target user information label described in (1) is affixed in any one of the following manners or in combination, as required; namely, a manner of the label being appended directly to a package, a manner of the label being appended to a floor at a location where commodities are arranged on display, and a manner of the label being appended to an article to be hung on shelves having the commodities arranged thereon. Thus, the target user information label affords convenience to an ordinary consumer when he purchases a commodity. Selection of one from or combination of the target user information labels is determined in accordance with the circumstances of retail dealers or manufacturers who append the target user information label, such as costs and exchange operations.

(3) Preferably, the target user information label described in (1) or (2) is highlighted in at least one manner selected from the group consisting of a "manner in which a predetermined target user design displayed in greater size than other target user designs being shown in a color different from the color of the other target user designs," a "manner in which a corresponding information notice is attached to a predetermined target user design displayed in greater size than other target user designs," and a "manner in which a sign for adjunctly rendering conspicuous a predetermined target user design which is displayed in greater size than other target user designs."

The invention described in (3) enables highlighting of a corresponding target user design from among the set of target user designs displayed, in a more conspicuous and readily perceivable manner. In connection with usage of a target user design; that is, assigning a different color to a predetermined target user design, attaching an information statement to a predetermined target user design, and appending a symbol to a predetermined target user design, even when a predetermined target user design is provided in solely any one of the above-described manners, there is yielded a corresponding effect (that is, an effect of enabling a user to readily perceive the design). Alternatively, when a predetermined target user design is displayed by use of the above-described manners in combination, a more conspicuous effect can be yielded.

As a more preferable manner of implementation of the invention described in (3), an "information statement corresponding to a predetermined target user design displayed in greater size than other target user designs" and a "sign for adjunctly rendering conspicuous a predetermined target user design displayed in greater size than other target user designs" are indicated in the vicinity of a target user design which is displayed in greater size than any other designs in a set of target user designs.

(4) Preferably, the target user information label described in any one of (1) through (3) is used with a series of commodities relating to disposable undergarments having absorbents.

It is considered that the majority of target users of the commodities according to the present invention are elderly people whose physical functions have become weakened and who face constraints on their personal mobility in daily life. Elderly people are considered to encounter difficulty in purchasing a commodity. According to the invention described in (4), an elderly person can quickly and correctly identify a desired commodity from analogous commodities. Thus, the present invention is very beneficial to elderly people.

(5) Preferably, the target user information label described in any one of (1) through (3) is used for commodities related to personal care products.

In connection with the invention described in (5), there are many similar care products. It is considered that an elderly person does not have the slightest idea about a personal care product suitable for himself (particularly, it is considered that an elderly person whose physical functions have become weakened fails to have the slightest idea about a suitable personal care product). The target user information label according to the present invention enables clear highlighting of a commodity for a target user of interest from among commodities of the same type. Hence, even an elderly person having weakened physical functions can very easily find a desired commodity from commodities arranged on display, without regard to whether or not the commodities pertain to a plurality of manufacturers or a single manufacturer.

(6) Preferably, the target user information label described in (5) is characterized in that the target user design comprises a set of target user designs arranged in descending order of necessity for assistance.

According to the invention described in (6), a person who attempts to purchase a commodity can readily decide the degree of care which a target user requires, at a glance. Through experience in purchasing a commodity several times, the user memorizes the layout of target user designs provided as a set. Subsequently, the user can diminish a chance of erroneously purchasing another commodity as a result of misidentification, by means of ascertaining the pattern of the set of overall target user designs. When a user of a certain commodity asks a third party to purchase the commodity, the only requirement imposed on the user is to inform the third party of only the size and position of a target user design; for example, a "commodity having a large design located at the $x^{th}$ position from the right." Thus, a unified view concerning a desired product can be shared between the user and the third party, thereby diminishing erroneous purchase of a commodity due to misidentification.

(7) The target user information label described in (5) or (6), wherein the target user design is displayed in conjunction with a design showing a care-giver when the target user design displays a person who needs assistance.

(8) The target user information label described in (7), wherein the design showing a person who needs assistance is displayed more conspicuous than a design showing the care-giver.

According to the invention described in (7), the target user design is displayed in conjunction with a design showing a care-giver when the target user design displays a person who needs assistance. Hence, a commodity product employing the target user design is obvious as to whether or not the product is intended for persons who need assistance. Particularly, according to the invention described in (8), the design showing a person who needs assistance is displayed more conspicuous than a design showing the care-giver. Accordingly, it is clearly understandable that a commodity product employing the target user design is intended for persons who need assistance.

(9) Preferably, the target user information label described in any one of (1) through (8) is characterized in that the target information design is formed from a design easy to memorize in association with a corresponding image.

According to the invention described in (9), even when a user views only an enlargedly-displayed target design, the user can perceive the target user of a commodity from the design. In addition, even when a user asks a third party to purchase a commodity, a chance of the third party erroneously purchasing another commodity is diminished.

(10) The target user information label described in any one of (1) through (9) is further characterized in that the target user design or the set of target user designs correspond (s) to registered trademark(s) (Section 18 of the Japanese Trademark Law).

According to the invention described in (10), the target user design and/or the set of target user designs can prevail all over Japan. Thereby, consumers can perceive the existence and significance of the design(s), thereby diminishing a chance of erroneous purchase of another commodity due to confusion with other commodities. If target user designs actually provided on commodities become widely known as a result of repeated use of the designs, the target user designs are protected from illegal use of the designs by illegal competitors. Moreover, when another person (business entity) is granted legal use of target user designs, the target user designs are used within the same category under the Japanese Trademark Law (Section 25 of the Japanese Trademark Law and Section 53 of the same). As a result, labels are unified within an industry, thereby preventing confusion due to use of different labels by other companies.

(11) A group of packages appended with the target user information label described in (1).

(12) The group of packages described in (11) is characterized in that the target user information label is appended to a position on an upper portion of a package where the label is easy to see.

According to the invention described in (12), even when a commodity formed by packing an object in a package is arranged for display on a shelf of a shop and a lower portion of the commodity is hidden behind a price tag, a purchaser can readily perceive and determine a desired commodity.

(13) Preferably, a group of commodities are packed with the package described in (11) or (12).

According to the invention described in (13), the present invention is applied to commodities which are packed in packages of substantially the same size and shape and which pose difficulty in identifying a desired commodity. Consequently, erroneous purchase of a commodity due to misidentification can be effectively diminished.

(14) Preferably, the group of commodities described in (13) is characterized in that commodities having enlarged target user designs of different types are arranged for display on shelves of a shop.

In a case where there are commodities intended for different users, the target user information label according to the present invention makes it very easy for an ordinary consumer to find desired commodities from commodities arranged on display. Even when a consumer views commodities from a slightly remote location, the consumer can identify the geometry of the overall set of target user designs (e.g., the location of a protuberance in the entire set of target user designs). Hence, the target user label matches the actual conditions under conditions from selection of a desired commodity to purchase of the thus-selected commodity product, thereby affording convenience to ordinary consumers. Difference between the effect of the related-art sign and the effect of the target user information label according to the present invention appears in the form of a noticeable difference in effects when commodities are actually arranged for display on shelves of a shop and ordinary consumers select suitable commodities from the shelves. Specifically, when the target user information label according to the present invention is used, ordinary consumers can very easily find suitable commodities. As mentioned previously, when a consumer views commodities on shelves from a slightly remote location, the ordinary consumer becomes substantially unable to select a suitable commodity. However, the present invention enables an ordinary consumer to select a suitable commodity.

(15) A color information mat to be used for commodities of the same type or analogous commodities whose target users are different is laid on a floor in the vicinity of a location where the commodities of the same type or the analogous commodities whose target users are different are to be arranged on display. A color identical in hue with the color used in the location for display is used for the color mat.

Here, the expression "identical in hue" basically means an "identical color." However, the expression is intended to allow slight difference in color.

As a result, an ordinary consumer can smoothly select a commodity by reference to a color, thereby affording convenience to the ordinary consumer. Further, colors are unified, which in turn results in realization of unified atmosphere in the location for display. In contrast with the case of a location for display having a disordered atmosphere, the colors afford to an ordinary consumer an impression of "ease of purchase" (i.e., an improvement in the environment of a location for display) Further, it can be expected that an increase in an appetite for shopping also contributes to an improvement in sales of a shop.

Definition of Terms

Throughout the specification, the expression "location for display" is narrower in concept than a so-called "selling section." For instance, when commodities are arranged on shelves, the locations of the shelves correspond to the location for display.

Throughout the specification, the expression "append" means that presence of a "target user information label" is made evident in any form in connection with an object commodity, without regard to the manner of appending, such as adhesion, drawing, or printing. Accordingly, if the target user information label can be visible to a consumer, the label is included in the concept of "append," so long as the label is in a visible state.

Throughout the specification, the expression "article to be hung" means a substance which is temporarily fixed or hung on a shelf.

Throughout the specification, the expression "disposable undergarments" means products which are manufactured and sold as "disposable commodities" such as paper diapers, regardless of length of service life or lifetime of the products.

Throughout the specification, the expression "display" means layout or arrangement of sales commodities which enables ordinary consumers and purchasers to view the commodities. For instance, when commodities are arranged on "shelves of a shop for display," commodities arranged on shelves, which shelves ordinary consumers cannot view, do not correspond to the state of "display" mentioned herein. In a case where commodities are arranged on shelves located at a position where ordinary consumers can view the commodities, the commodities are included in the concept of "display" described herein without regard to the layout, sequence of arrangement, and geometry of commodities placed on shelves, so long as the commodities are arranged so as to be visible for ordinary consumers in any form.

Throughout the specification, the expression "ordinary consumers and purchasers" encompasses persons who have not yet actually consumed or purchased commodities but who merely have an intention of consuming or purchasing commodities, as well as persons who have actually consumed or purchased commodities.

Throughout the specification, the expression "a symbol for adjunctly rendering conspicuous a predetermined target user design" includes, for example, a sign or symbol appended to the vicinity of a predetermined target user design, as well as an "arrow."

BRIEF DESCRIPTION OF THE DRAWINGS

FIG. 4(B) is an illustration for describing a case where a rail 21a of a shelf is assigned color by means of causing a color panel 31 to engage with the rail 21a;

FIGS. 5(A) through 5(E) are illustrations showing target user designs employed in a target user information label, wherein

FIGS. 11(A) and 11(B) are plan views showing preferable target user information pointers 25 to be used as an article to be hung on the commodity shelves 21, wherein FIG. 11(A) is a pointer oriented to the left side, and FIG. 11(B) is a pointer oriented to the right side.

DETAILED DESCRIPTION OF THE PREFERRED EMBODIMENTS

Preferred embodiments of the present invention will now be described by reference to the accompanying drawings. The present embodiment is described by means of taking a paper diaper as a disposable undergarment having an absorbent. Details of a target user information label according to the present invention can be changed freely in accordance with the types of commodities. It is evident that the present invention can be applied to items other than a paper diaper. Although a paper diaper is described as a preferable embodiment of the invention, the present invention is not limited to a paper diaper, a package having paper diapers packed therein, and a target user information label to be affixed on the surface of the package.

Overall Configuration of a Package

Figure 1:
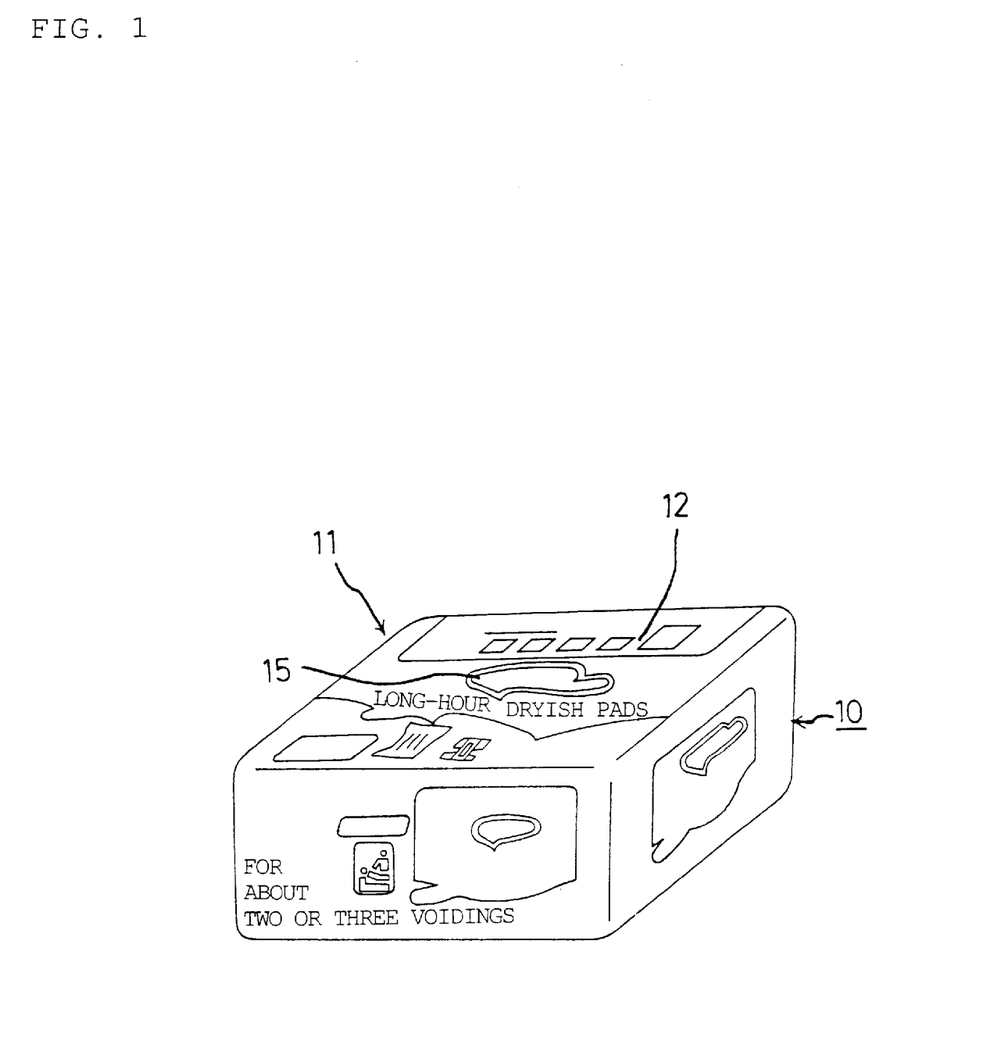
FIG. 1 is a perspective view showing the principal part of a package of a paper diaper according to an embodiment of the present invention, showing one commodity among commodities whose target users are different.
Figure 2:
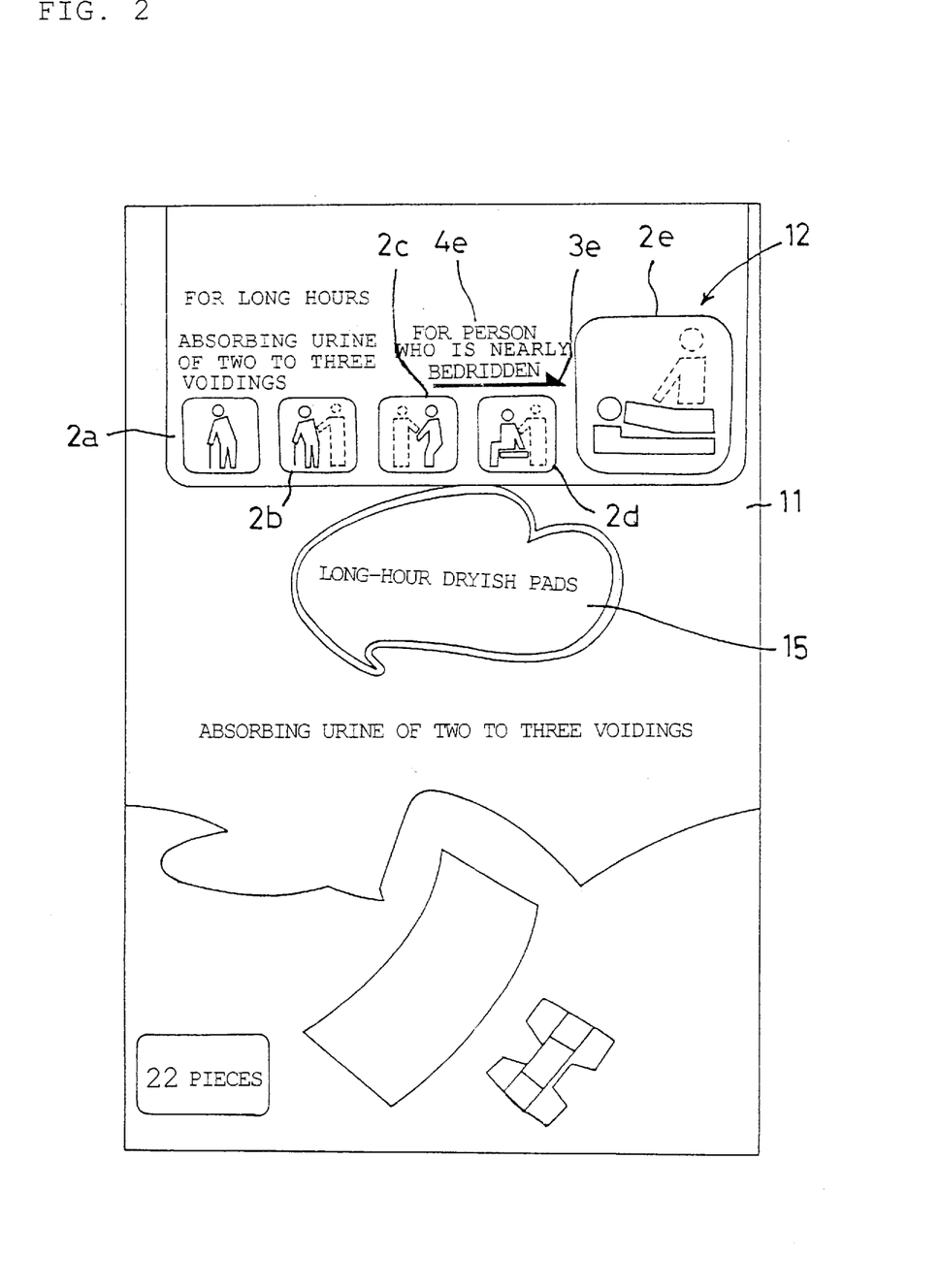
FIG. 2 is an explanatory view for describing details of a label affixed to an upper portion of a package 11 according to the present embodiment.

FIG. 1 is an illustration showing a preferred embodiment of the present invention. FIG. 1 is a schematic perspective view showing a packaged product 10 in which unillustrated paper diapers are packed with a package 11. FIG. 2 shows a front view of the packaged product 10 in more detail.

Here, paper diapers assumed to be used in the present embodiment are to be offered to an elderly person who faces constraints on his or her personal mobility in daily life and requires assistance. In connection with those paper diapers, the amount of absorbent the structure and thickness of the paper diapers are different from each other in accordance with the degree of assistance in which the target user requires. However, the packaged products 10, each packed with the package 11, finally assume substantially the same structure. Hence, a trade name 15 of a paper diaper or uses of the paper diaper are printed on the surface of the package 11 for enabling distinction of the packaged products 10 from other packaged products.

The packaged product 10 according to the present invention has printed thereon the trade name 15 of a paper diaper, uses of the paper diaper, and a target user information label section 12 serving as a target user information label according to the present invention. As a matter of course, a target user design corresponding to the target user of paper diapers to be packed in the package 11 is to be printed in the information label section 12. In a preferred embodiment, the information label section 12 is printed simultaneously with printing of the trade name 15 and uses of paper diapers. In a more preferred embodiment, the information label section 12 is printed at a conspicuous position on an upper portion of the packaged product 10 such that the information label section 12 is not hidden behind a rail 21a [see FIG. 4(A)] when the packaged product 10 is placed on a commodity shelf 21 shown in FIG. 3 and such that the information label section 12 comes into the view of ordinary consumers (see FIGS. 1 and 2).

Figure 3:
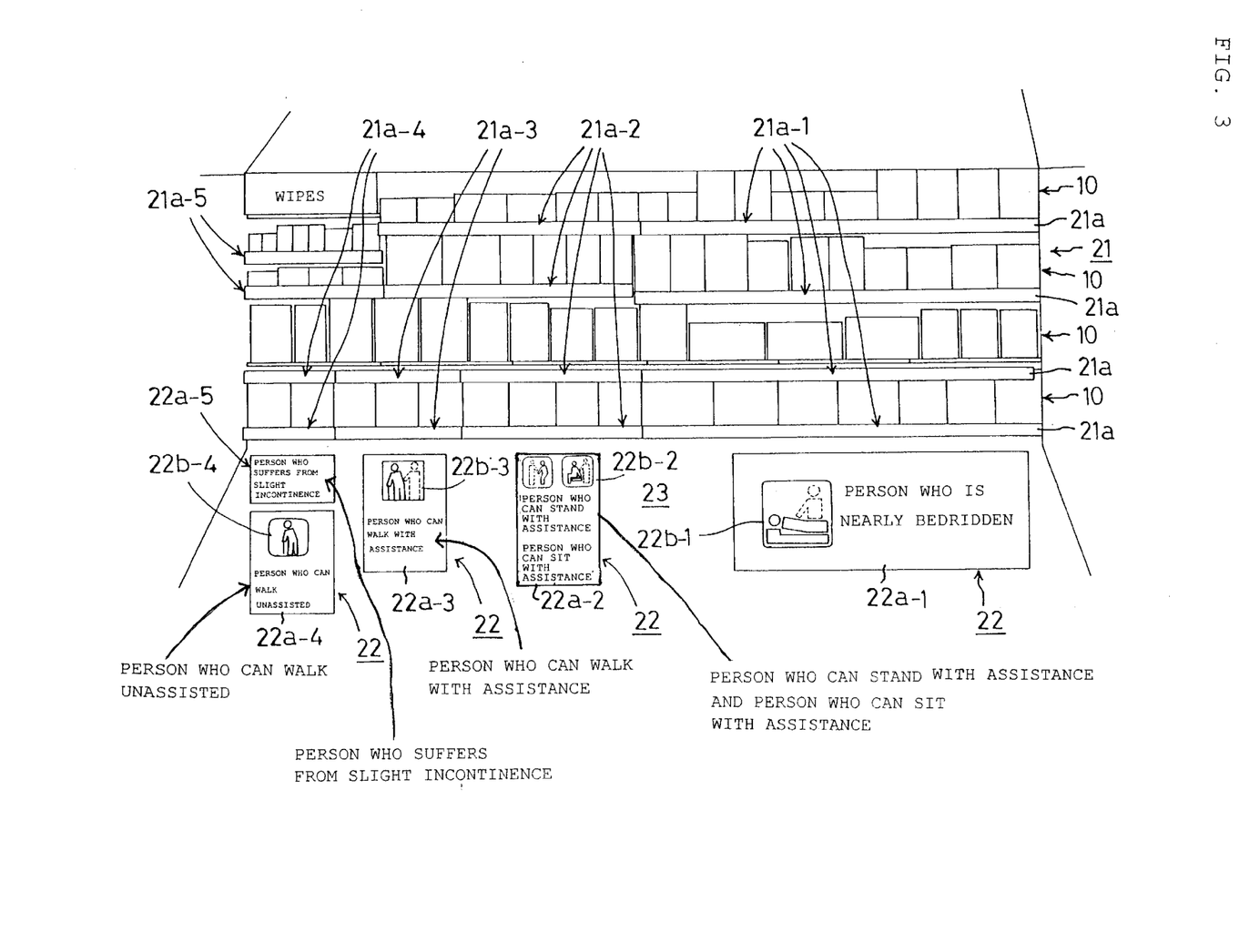
FIG. 3 is a view showing a case where a target user information label is embodied as information mats for target users 22 and where the mats 22 are placed on a floor 23 in the immediate lower vicinity of commodity shelves 21.
Figure 4A:
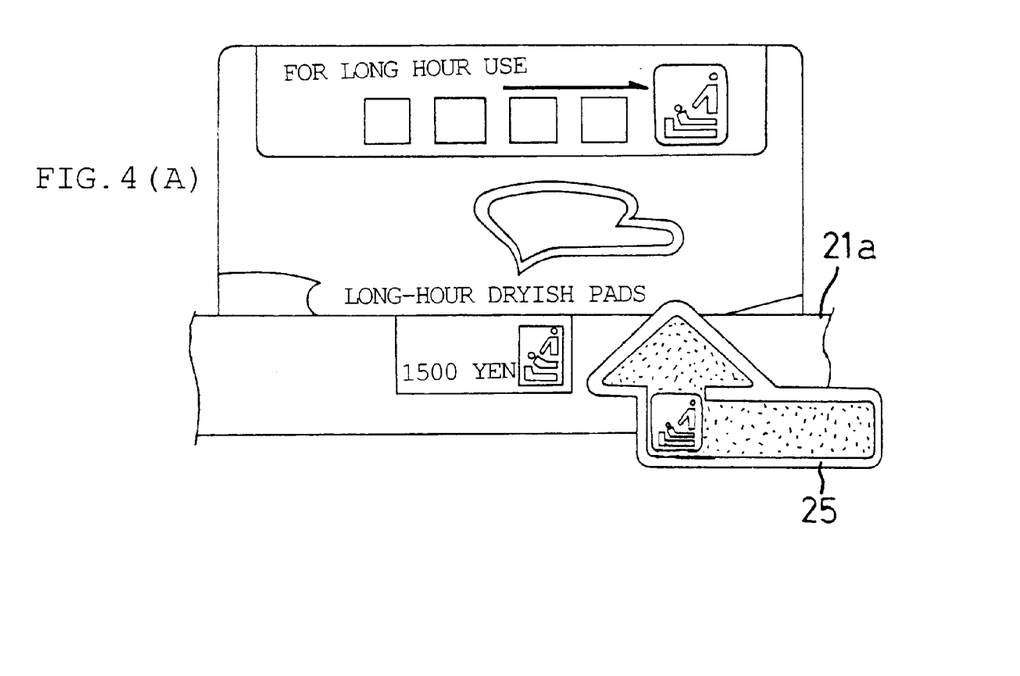
FIG. 4(A) is an illustration for describing a case where a target user information label according to the present invention is embodied as a target user information pointer 25; that is, an article to be hung on the commodity shelves 21.

The target user information label according to the present invention is appended to a conspicuous location on an upper portion of the packaged product 10. Therefore, even when an ordinary consumer views commodities placed on the shelves 21 from a slightly remote location, the information labels provided on the commodities immediately come into the consumer's view. As shown in FIG. 3, a target user information label according to the present invention is embodied as a target user information mat 22, and the information mat 22 is laid on a floor 23 in the immediate lower vicinity of the commodity shelves 21 (i.e., on a floor in the vicinity of the shelves). Such an information mat 22 acts as a very useful information source for an elderly person who is hunchbacked and has difficulty in looking upward. Further, as shown in FIG. 4(A), a target user information label according to the present invention is embodied as the target user information pointer 25 to be used as an article to be hung on the shelves 21. As a result, the pointer 25 adjunctly renders conspicuous the information label section 12 which serves as a target user information label to be appended to the package 10.

Specific Embodiment of Target User Information Label

As mentioned above, the information label section 12 serving as a target user information label according to the present invention is provided at an easily-visible position on the upper portion of the package 11. The pointer 25 is provided at an easily-visible position on the rail 21a of the shelf 21, and the mat 22 is placed at an easily-visible position in the immediate lower vicinity of the shelf 21. As a result, the information label section 12, the pointer 25, and the mat 22 are conspicuous to ordinary consumers' eyes.

The target user information label according to the present invention comprises a set of target user designs symbolically representing target users. Respective target user designs suggest or explicitly show the degree of personal mobility of a target elderly person in daily life. Simultaneously, the target user designs suggest or explicitly show the degree of assistance in which the target elder person requires assistance from a caregiver. In association with images of the degree of care, the target user designs are easily memorized by a person who attempts to purchase a commodity. Specific embodiments of a target user information label according to the present invention are now described.

Figure 5A:
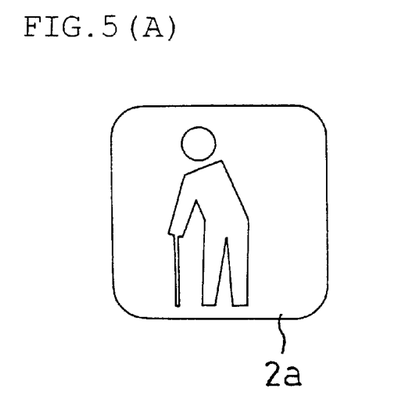
FIG. 5(A) is an illustration showing a target user design intended for a person who uses a paper diaper and can walk unassisted.
Figure 5B:
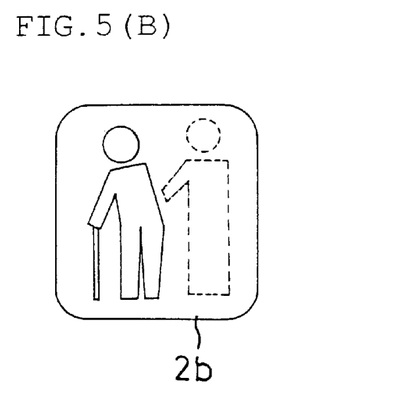
FIG. 5(B) is an illustration showing a target user design intended for a person who uses a paper diaper and can walk with assistance.
Figure 5C:
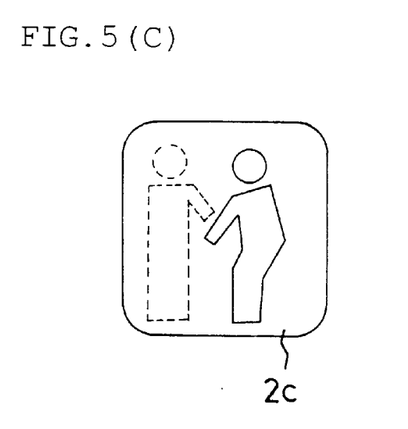
FIG. 5(C) is an illustration showing a target user design intended for a person who uses a paper diaper and can stand up with assistance.
Figure 5D:
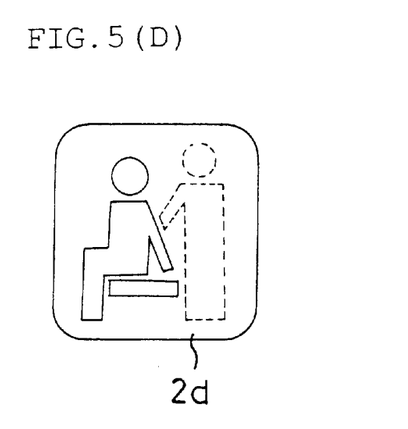
FIG. 5(D) is an illustration showing a target user design intended for a person who uses a paper diaper and can sit with assistance.
Figure 5E:
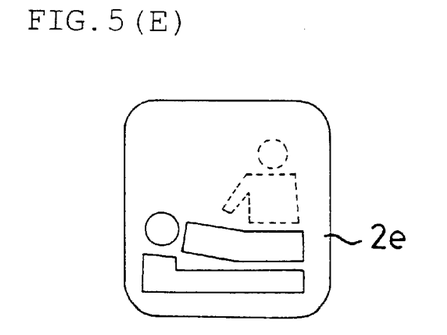
FIG. 5(E) is an illustration showing a target user design intended for a person who uses a paper diaper and is nearly bedridden.

FIGS. 5(A) through 5(E) are illustrations showing target user designs employed in a target user information label. A target user design 2a shown in FIG. 5(A) is a mark intended for a person who uses a paper diaper and can walk unassisted. A target user design 2b shown in FIG. 5(B) is a mark intended for a person who uses a paper diaper and can walk with assistance. A target user design 2c shown in FIG. 5(C) is a mark intended for a person who uses a paper diaper and can stand up with assistance. A target user design 2d shown in FIG. 5(D) is a mark intended for a person who uses a paper diaper and can sit with assistance. A target user design 2e shown in FIG. 5(E) is a mark intended for a person who uses a paper diaper and is nearly bedridden.

Here, in the target user design 2b (representing a person who needs assistance) shown in FIG. 5(B), there is provided a design showing a person who can walk with assistance in conjunction with a design showing a "care-giver" through use of broken lines. In the target user design 2c (representing a person who needs assistance) shown in FIG. 5(C) there is provided a design showing a person who can stand up with assistance in conjunction with a design showing a "care-giver" through use of broken lines. In the target user design 2d (representing a person who needs assistance) shown in FIG. 5(D), there is provided a design showing a person who can sit with assistance in conjunction with a design showing a "care-giver" through use of broken lines. In the target user design 2e (representing a person who needs assistance) shown in FIG. 5(E), there is provided a design showing a person who is nearly bedridden in conjunction with a design showing a "care-giver" through use of broken lines. Thus, the designs showing persons who need assistance are displayed more conspicuously than the design showing a "care-giver."

In the present embodiment, a design showing a "care-giver" is displayed through use of broken lines. The broken lines are employed for a patent application document in which a color display is not allowed. Essentially, displaying the designs in colors so as to become distinguished from each other is preferable. When the design showing a "care-giver" is displayed in color, the design showing a care-giver is displayed in a color different from that in which a design showing a "person who needs assistance" is displayed. The design showing a "care-giver" is displayed in a color analogous to a background color of the target user designs 2b through 2e (e.g., the background is displayed in dark vermilion, and the design showing "care-giver" is displayed in light vermilion). Further, designs showing "persons who need assistance" are displayed in color (e.g., white) contrary to the background color. As a result, displaying the designs showing "persons who need assistance" more conspicuously than a design showing a "care-giver" can be implemented.

As a matter of course, the present invention is not limited to these examples. Any means can be employed such as the lines shown in FIGS. 5(B) through 5(E), so long as the means can distinguish "persons who need assistance" from a "care-giver."

Figure 6:
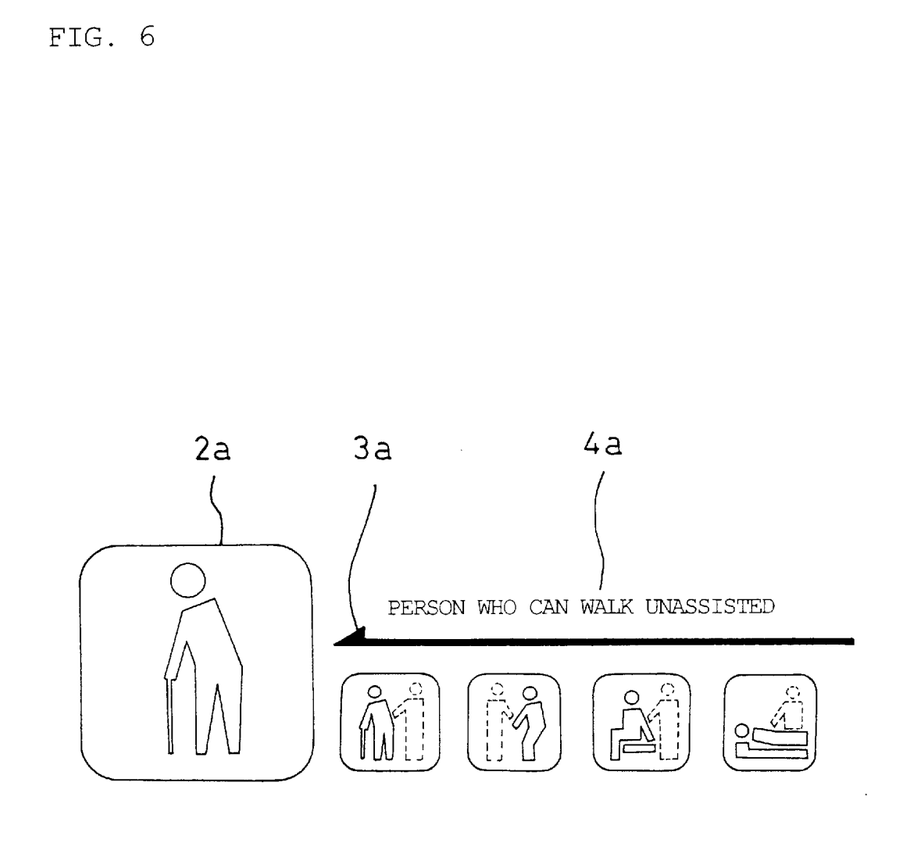
FIG. 6 is an illustration for describing a set of target user designs employed in a target user information label according to the present embodiment, wherein a target user design intended for a person who can walk unassisted is taken as a predetermined target user design.
Figure 7:
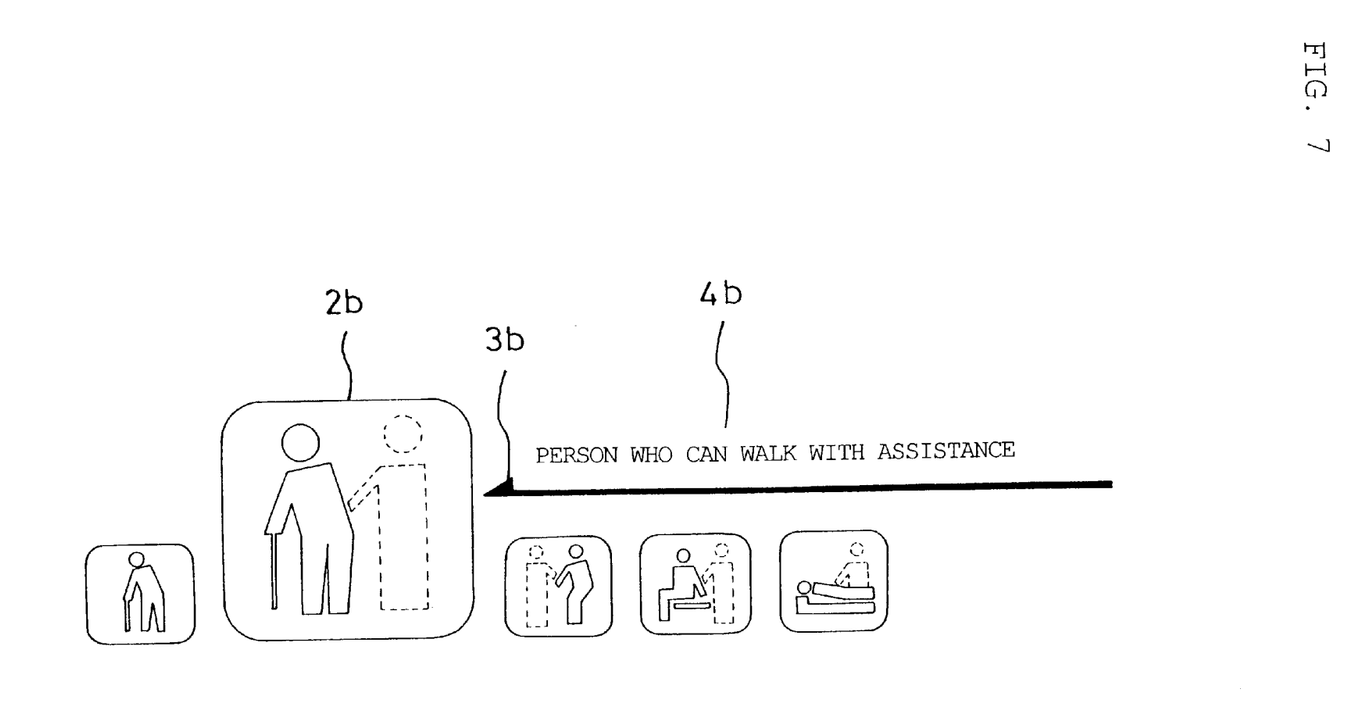
FIG. 7 is an illustration for describing a set of target user designs employed in a target user information label according to the present embodiment, wherein a target user design intended for a person who can walk with assistance is taken as a predetermined target user design.
Figure 8:
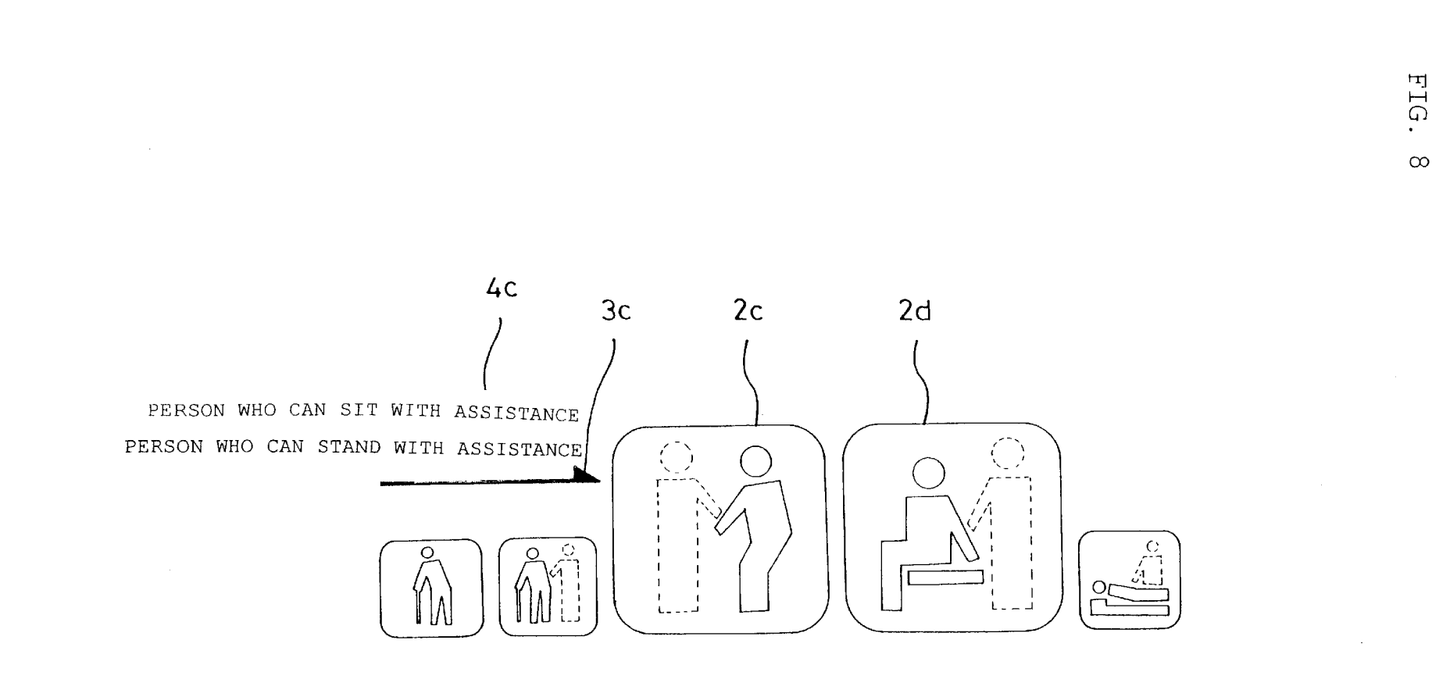
FIG. 8 is an illustration for describing a set of target user designs employed in a target user information label according to the present embodiment, wherein a target user design intended for a person who can stand with assistance and for a person who can sit with assistance" are taken as predetermined target user designs.
Figure 9:
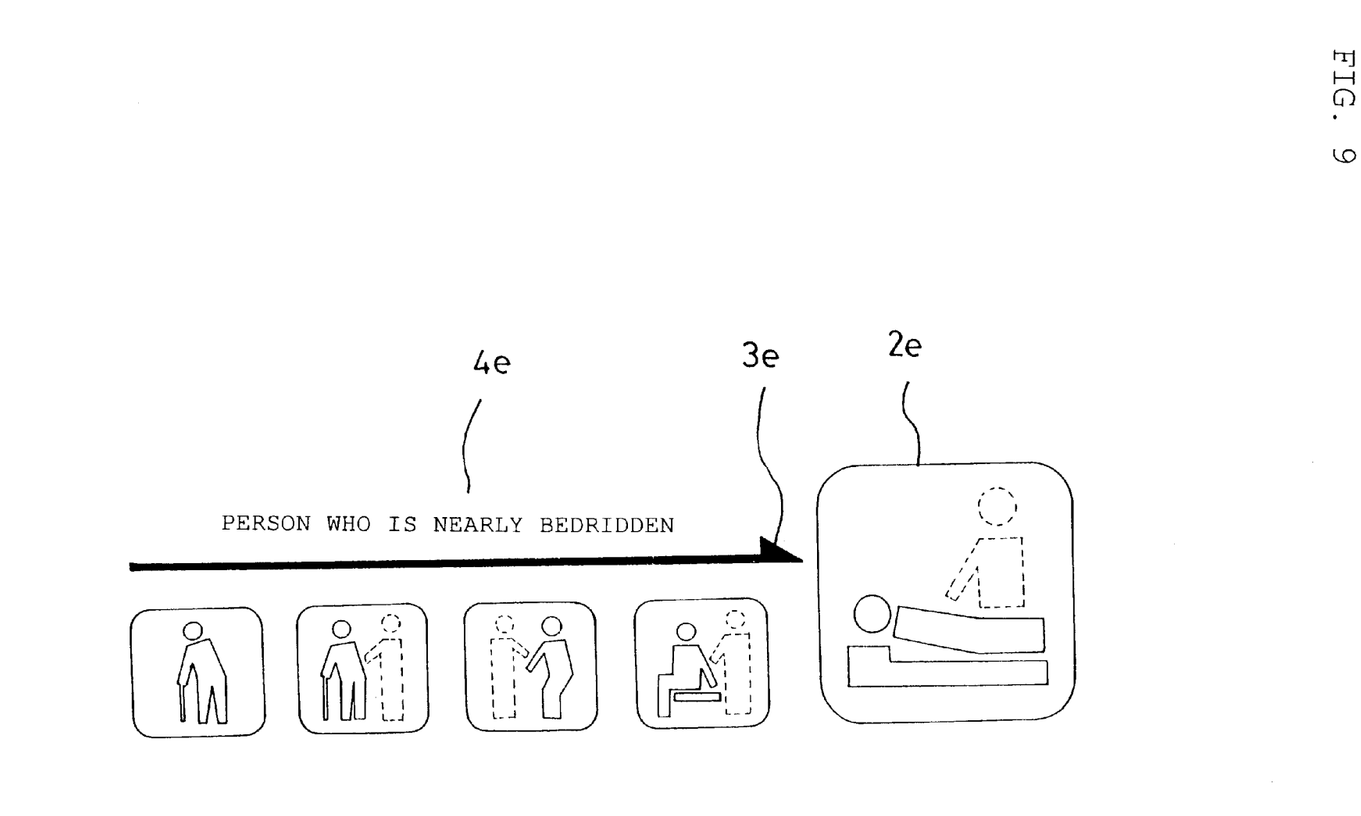
FIG. 9 is an illustration for describing a set of target user designs employed in a target user information label according to the present embodiment, wherein a target user design intended for a person who is nearly bedridden is taken as a predetermined target user design.

FIGS. 6 through 9 are descriptive illustrations for describing a set of target user designs related to a target user information label according to the present embodiment. FIG. 6 shows a set of target user designs, wherein the target user design 2a intended for a person who can walk unassisted is enlargedly displayed as a predetermined target user design. FIG. 7 shows a set of target user designs, wherein the target user design 2b intended for a person who can walk with assistance is enlargedly displayed as a predetermined target user design. FIG. 8 shows a set of target user designs, wherein the target user designs 2c and 2d intended for a person who can stand with assistance and for a person who can sit with assistance are enlargedly displayed as predetermined target user designs. FIG. 9 shows a set of target user designs, wherein the target user design 2e intended for a person who is nearly bedridden is enlargedly displayed as a predetermined target user design.

As illustrated, in connection with target user information labels according to the present invention, all the target user designs corresponding to all the target users of a line of paper diapers to be handled as a commodity are displayed as a set. A target user design corresponding to a target user of paper diapers packed in the package 11 is displayed greater in size than the other target user designs provided in the set.

As a result, a person who attempts to purchase a commodity can understand a category in which the commodity is sold. Further, an ordinary consumer can perceive at a glance that a target user of packed paper diapers is a person who can walk unassisted.

In the present embodiment, in FIG. 6, an arrow 3a is attached to the target user design 2a as a symbol for adjunctly rendering the target user design 2a conspicuous. Further, a statement 4a reading "Person who can walk unassisted" corresponding to the target user design 2a is displayed. Although FIG. 6 poses difficulty in perceiving colors, the target user design 2a is actually printed in red in contrast with the other target user designs printed in blue. Thus, the target user design 2a is more conspicuous than the other target user designs, by virtue of color.

In FIG. 7, the target user design 2b is displayed in red and greater in size than the other target user designs displayed in blue, so that an ordinary consumer can perceive at a glance that a target user of packed paper diapers is a person who can walk with assistance. The target user design 2b is assigned an arrow 3b serving as an adjunctive symbol and an information statement 4b reading a "person who can walk with assistance."

In FIG. 8, two target user designs 2c and 2d are displayed in red and greater in size than the other target user designs displayed in blue, so that an ordinary consumer can perceive at a glance that target users of packed paper diapers are a person who can stand up with assistance and a person who can sit with assistance. The target user designs 2c and 2d are assigned a common arrow 3c serving as an adjunctive symbol, and an information statement 4c reading a "person who can stand up with assistance or sit with assistance." The present invention is embodied such that a plurality of target user designs are displayed greater in size than the other target user designs, as well as such that only the target user design(s) for the commodity in the package 11 is (are) enlargedly displayed. Thus, great convenience is afforded to manufacturers who manufacture commodities.

In FIG. 9, the target user design 2e is displayed in red and greater in size than the other target user designs displayed in blue, so that an ordinary consumer can perceive at a glance that a target user of packed paper diapers is a person who is nearly bedridden. The target user design 2e is assigned an arrow 3e serving as an adjunctive symbol, and an information statement 4e reading a "person who is nearly bedridden."

In the embodiments shown in FIGS. 6 through 9, the target user information label is formed such that a set of target user designs constituting the label are arranged in descending order of degree of assistance required. Hence, a purchaser can perceive at a glance the location of commodities suitable for the purchaser and the degree of required care. In addition, ordinality exists in the order in which target user designs are arranged. Hence, the user can readily memorize all the target user designs belonging to the set, by means of ascertaining the pattern of the set of overall target user designs. Moreover, so long as a purchaser memorizes the target user designs, there can be diminished a chance of the purchaser erroneously purchasing another commodity due to misidentification.

Further, so long as the target user designs specifically constituting the target user information label according to the present invention and/or the set of target user designs are registered as trademarks, ordinary consumers' confusion about target user information labels, which would otherwise be caused by illegal use of the target user designs by illegal competitors, can be prevented even when the target user designs will have become prevalent.

Additional Configuration

As shown in FIG. 2, the capacity of absorbent "capable of absorbing urine released in two to three voidings" and the lifetime "e.g., long hour use" are displayed on the surface of the package 11. Further, a trade name 15 "Long-hour Dryish Pads" is displayed in the center portion of the package 11. Simple illustrations representing a product, the name of the manufacturer, and the number of paper diapers packed in the package 11 (i.e., "22 sheets") are displayed in a lower portion of the package 11.

However, the typical construction of the package 11 according to the present invention is as follows: A set of target user designs are printed as the information label section 2, at a position most easily viewable for a purchaser on an upper portion of the package 11. The target user design 2e serving as a predetermined target user design is displayed in red and greater in size than the other target user designs 2a through 2d displayed in blue. Further, the target user design 2e is assigned an arrow 3e serving as an adjunctive symbol, and an information statement 4e reading "person who is nearly bedridden."

Figure 10:
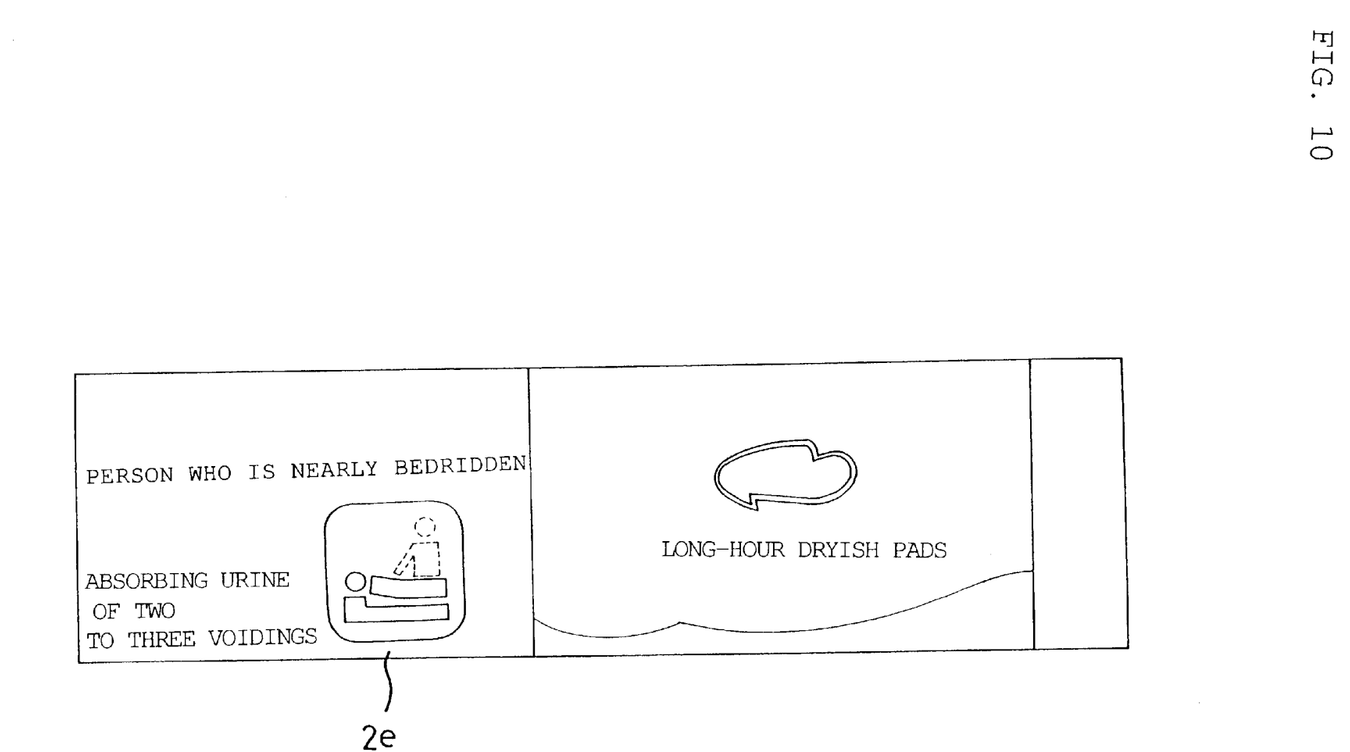
FIG. 10 is an explanatory illustration for describing details of a label affixed on a front section of the package 11 according to the present embodiment.

In the present invention, a target user information label is displayed at a very-noticeable position on an upper portion in the vicinity of the position where the trade name is displayed, in preference to other information to be printed, thereby enabling a consumer to perceive at a glance a target user of the commodity. As shown in FIG. 10, solely the specific target user design 2e belonging to the set of target user designs constituting the target user information label according to the present invention is displayed on a front section of the package 11 according to the embodiment. As a result, a target user design corresponding to the target user of packed paper diapers can be made recognizable from as many angles as possible. Even when the packages 11 are stacked vertically for display and many commodities are provided for display in an overlapping manner, there can be diminished a chance of occurrence of erroneous purchase of another commodity, which would otherwise be caused by misidentification.

In the present embodiment, the present invention has been described, by means of taking as an example a display package having packed therein commodities of the same type or analogous commodities whose target users are different and having a target user information label. However, the present invention is not limited to such an example. The target user information label according to the present invention can be provided on a floor in the vicinity of shelves on which are to be placed commodities of the same type or analogous commodities whose target users are different. For instance, when commodities are placed on shelves, the information label is provided on the floor in the vicinity of the shelves. When commodities are placed directly on a floor while being held in a corrugated cardboard carton as is often the case in a discount shop, it goes without saying that the information label is provided on the floor in the vicinity of the commodities on display.

Figure 11A:
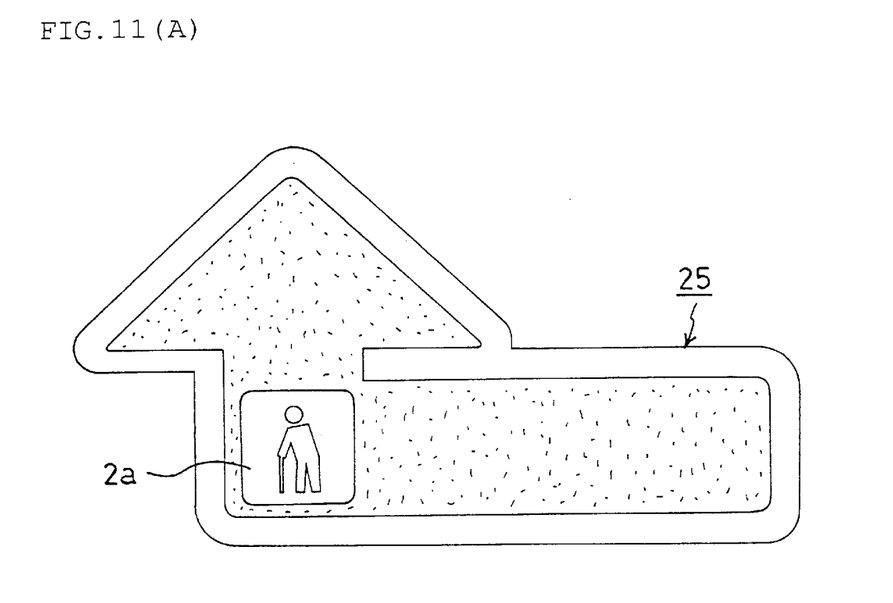
Figure 11B:
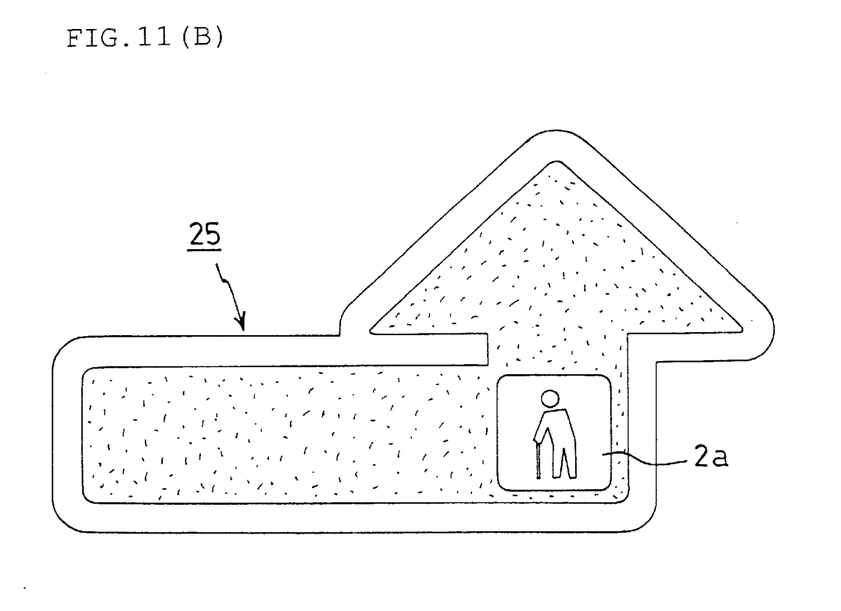

As has been described by reference to FIG. 4(A), the target user information label according to the present invention can be embodied as the target user information pointer 25 and hung on the rail 21a of the shelves 21. As shown in FIGS. 11(A) and 11(B), solely the specific target user design 2a (of the set of target user designs constituting the target user information label) is displayed on the surface of a bent-arrow-shaped plate. The pointer 25 may be provided as an article to be hung on a shelf. Alternatively, a target user information label may be provided on a name plate having descriptions above a commodity or on a tag specifically designed for providing information [see FIG. 4(A)]. Here, an article to be hung is not limited to an article to be hung directly on a shelf, but may be an article to be hung directly on a commodity or a ceiling.

Manners of Appending a Label

As has been described, in the present embodiment a target user information label is "appended" to a package by means of direct printing. However, the information label may be printed on a peel-off sticker, and the sticker may be affixed to the package. Alternatively, the information label may be drawn directly on the package. In any event, the target user information label according to the present invention can be susceptible to various uses, thereby rendering the information label visible for consumers. As a result, existence of the information label becomes evident, thereby exhibiting its original effect.

In the present embodiment, a predetermined target user design corresponding to the target user of packed paper diapers is printed in red, while the other target user designs are printed in blue. A statement reading "Person who can walk unassisted" is described as an information statement corresponding to the predetermined target user design. Moreover, the target user design is assigned an arrow as an adjunctive symbol for rendering the predetermined target user design conspicuous. The present invention can yield an effect so long as the present invention is implemented in any one of the following manners; that is, displaying the target information labels in different colors, appending an information statement to a predetermined target information label, and assigning a symbol to a predetermined target information label. Although in the present embodiment an arrow is employed as an adjunctive symbol, various symbols may be employed, so long as the symbols highlight a predetermined target user design, such as an annular symbol.

Improvements in the Environment of Shelves

In the present embodiment, four information mats 22 for target user are provided. As shown in FIG. 3, the respective four mats 22 are provided with a target display section 22b-1 corresponding to the target user design 2e as shown in FIG. 2, a target display section 22b-2 corresponding to the target user designs (2d+2c) as shown in FIG. 2, a target display section 22b-3 corresponding to the target user design 2b as shown in FIG. 2, and a target display section 22b-4 corresponding to the target user design 2a as shown in FIG. 2. The areas of the mats 22 other than the target display sections 22b-1, 22b-2, 22b-3, and 22b-4 constitute color information sections 22a-1, 22a-2, 22a-3, and 22a-4. Explanatory descriptions, such as "Person who can walk unassisted, "Person who can walk with assistance," "Person who can stand with assistance and sit with assistance," and "Person who is bedridden," are provided in the respective color information sections 22a-1 through 22a-4. Moreover, a color information mat 22a-5 has only a description "Person who suffers from slight incontinence," and no target user display section is provided in the mat.

Figure 4B:
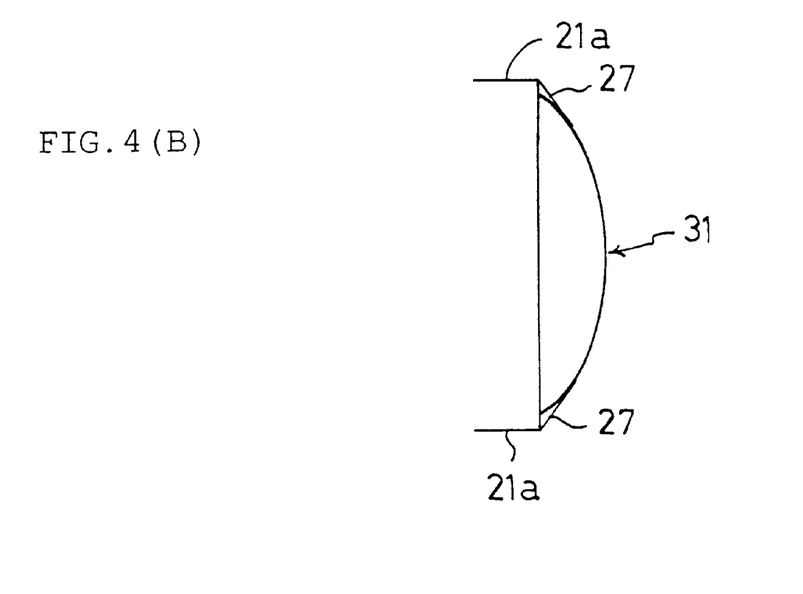

As shown in FIG. 4(B), the rail 21a of the shelf 21 is provided with a pair of locking lugs 27 at the top and the bottom. An elongated color panel 31 is held by the locking lugs 27.

In this state, the characteristic of the present invention lies in that the rail 21a-1 of the shelf 21 having placed thereon commodities intended for, for example, "Person who is nearly bedridden" and the color information section 22a-1 of the target user information mat 22 appear in the same color; that is, red. (See FIG. 3)

Similarly, the rail 21a-2 of the shelf 21 having placed thereon commodities intended for "Person who can stand with assistance and sit with assistance" and the color information section 22a-2 of the mat 22 both appear in blue. The rail 21a-3 of the shelf 22 having placed thereon commodities intended for "Person who can walk with assistance" and the color information section 22a-3 of the mat 22 both appear in pink. The rail 21a-4 of the shelf 21 having placed thereon commodities intended for "Person who can walk unassisted" and the color information section 22a-4 of the mat 22 both appear in green. The rail 21a-5 of the shelf 21 having placed thereon commodities intended for "Person who suffers from slight incontinence" and the mat 22a-5 having a description "Person who suffers from slight incontinence" both appear in yellow.

The colors of the rails 21a-1 through 21a-5 of the shelf 21 are adjusted, by means of modifying the color of the color panel 31.

As a result, an ordinary consumer can smoothly select a desired commodity by reference to a color, thereby affording convenience to ordinary consumers. Since colors are unified, ordinary consumers realize a unified atmosphere in the location for display. In contrast with the case of a location for display having a disordered atmosphere, the colors afford to an ordinary consumer an impression of "ease of purchase" (i.e., an improvement in the environment of a location for display). Further, it can be expected that an increase in an appetite for shopping also contributes to an improvement in sales of a shop.

In the previous embodiment, the present invention has been described by taking paper diapers serving as disposable undergarments as examples of commodities related to personal care products. However, the present invention is not limited to such examples and can be applied to ordinary apparel products.

As has been described, according to the present invention, when there are commodities of the same type or analogous commodities whose target users are different, a predetermined target user design of a set of target user designs is displayed greater in size than the other target user designs. Hence, a corresponding target user is clearly pointed out, and an ordinary consumer can immediately find a desired commodity from commodities placed on shelves for display.

For example, even a purchaser who is an ordinary consumer and physically handicapped to such an extent that he requires care from another person can discern at a glance a commodity suitable for his current status. Thus, convenience in purchasing a commodity is afforded to a handicapped consumer.

What is claimed is:

1. A package having an exterior, said package comprising:
   a commodity; and
   a target user information label on said exterior for identifying said commodity as a type of commodity within a group of analogous types of commodities,
   wherein said label comprises a first target user picture illustrating first human target users of a first type of commodity within the group of analogous types of commodities and a second target user picture illustrating second human target users of a second type of commodity within the group of analogous types of commodities,
   wherein said first target user picture is larger than said second target user picture when said commodity is of said first type of commodity, and wherein said second target user picture is larger than said first target user picture when said commodity is of said second type of commodity.

2. A group of packages, each of which has an exterior, at least one of said packages comprising a commodity and a target user information label which is disposed on said exterior for identifying said commodity as a type of commodity within a group of analogous types of commodities;

wherein said label comprises a first target user picture illustrating first human target users of a first type of commodity within the group of analogous types of commodities and a second target user picture illustrating second human target users of a second type of commodity within the group of analogous types of commodities, wherein said first target user picture is larger than said second target user picture when said label is associated with said first type of commodity.

3. The group of packages according to claim 2, wherein said target user information label is appended to a position on an upper portion of the package so that said label is easily seen.

4. A package comprising an absorbent article, said package having a label appended thereto, wherein said label comprises a first design depicting a person being assisted with standing or walking and a second design depicting a person being in repose, and wherein one of said designs is enlarged relative to the other of said designs to indicate a target user of the absorbent article.

5. A commodity display comprising:

a first type of commodity within a group of analogous commodities;

a shelf for holding and displaying said first type of commodity; and a floor mat disposed in a proximity of said shelf and having a target user picture disposed thereon, wherein said target user picture illustrates a target user of said first type of commodity, and wherein a color of said floor mat is the same as a color of one of said first type of commodity and said shelf.

* * * * *